US009488504B2

(12) United States Patent
Wang

(10) Patent No.: US 9,488,504 B2
(45) Date of Patent: *Nov. 8, 2016

(54) ELECTRONIC DEVICE MOISTURE INDICATORS

(71) Applicant: Apple Inc., Cupertino, CA (US)

(72) Inventor: Erik L. Wang, Redwood City, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/804,070

(22) Filed: Jul. 20, 2015

(65) Prior Publication Data

US 2016/0012756 A1  Jan. 14, 2016

Related U.S. Application Data

(60) Continuation of application No. 13/868,821, filed on Apr. 23, 2013, now Pat. No. 9,086,298, which is a division of application No. 12/472,192, filed on May 26, 2009, now Pat. No. 8,440,274.

(51) Int. Cl.
*G01D 7/00* (2006.01)
*B32B 5/06* (2006.01)
(Continued)

(52) U.S. Cl.
CPC ............ *G01D 7/005* (2013.01); *B32B 5/06* (2013.01); *B32B 5/14* (2013.01); *G01D 7/00* (2013.01); *G01N 31/222* (2013.01); *G06F 1/1626* (2013.01); *G06F 1/1656* (2013.01); *G09F 3/0291* (2013.01); *H04M 1/0274* (2013.01); *H04M 1/18* (2013.01); *Y10T 428/13* (2015.01); *Y10T 428/1303* (2015.01); *Y10T 428/1352* (2015.01); *Y10T 428/1379* (2015.01); *Y10T 428/24612* (2015.01); *Y10T 428/24942* (2015.01); *Y10T 428/249953* (2015.04);
(Continued)

(58) Field of Classification Search
CPC ... G09F 3/0291; G01D 7/005; G06F 1/1626; G06F 1/1656; Y10T 428/1352; Y10T 428/1355; Y10T 428/1359; Y10T 428/1379; Y10T 428/1383; Y10T 428/31971
See application file for complete search history.

(56) References Cited

U.S. PATENT DOCUMENTS 8,440,274 B2 *   5/2013   Wang ................... G09F 3/0291
                                                     379/437
9,086,298 B2 *   7/2015   Wang ................... G09F 3/0291
9,300,773 B2 *   3/2016   Mittleman .......... H04M 1/0274

FOREIGN PATENT DOCUMENTS

EP         1 001 264       *   5/2000

*Primary Examiner* — Walter B Aughenbaugh
(74) *Attorney, Agent, or Firm* — Treyz Law Group, P.C.; G. Victor Treyz; Joseph F. Guihan

(57) ABSTRACT

Electronic devices may have sensitive circuitry. To determine whether an electronic device has been exposed to excessive amounts of moisture, the electronic device may be provided with a moisture indicator. The moisture indicator may have a wicking layer of white paper and a red dye layer. If a portion of the moisture indicator is exposed to moisture, red dye may bleed into the white paper. The moisture indicator may be mounted in an input-output port opening or other portion of the electronic device where the state of the moisture indicator is visible. The moisture indicator may have sealed edges to reduce sensitivity to small amounts of moisture intrusion. Different regions of the moisture indicator may be provided with different sensitivities by forming structures that have altered moisture flow properties, by altering wicking layer thicknesses, or by otherwise spatially modifying moisture sensitivity.

20 Claims, 21 Drawing Sheets

(51) Int. Cl.
*B32B 5/14* (2006.01)
*G06F 1/16* (2006.01)
*G01N 31/22* (2006.01)
*G09F 3/00* (2006.01)
*H04M 1/02* (2006.01)
*H04M 1/18* (2006.01)

(52) U.S. Cl.
CPC . *Y10T428/31786* (2015.04); *Y10T 428/31971* (2015.04); *Y10T 428/31993* (2015.04)

EXPOSURE TO MOISTURE

ELECTRONIC DEVICE MOISTURE INDICATORS

This application is a continuation of patent application Ser. No. 13/868,821, filed Apr. 23, 2013, now U.S. Pat. No. 9,086,298, which is a division of patent application Ser. No. 12/472,192, filed May 26, 2009, now U.S. Pat. No. 8,440,274, all of which are hereby incorporated by reference herein in their entireties. This application claims the benefit of and claims priority to patent application Ser. No. 12/472,192, filed May 26, 2009, and patent application Ser. No. 13/868,821, filed Apr. 23, 2013, now U.S. Pat. No. 8,440,274.

BACKGROUND

This invention relates generally to electronic devices, and more particularly, to moisture indicators for electronic devices.

Many electronic devices are susceptible to damage when exposed to excessive moisture. Large stationary devices such as televisions and desktop computers can typically be located in an area of a user's home or office where the likelihood of exposure to liquids can be reduced. For example, a television can be located in a safe environment such as a user's living room, rather than in an outdoors location where the television might be exposed to rain.

Safeguarding other electronic devices can be more difficult. For example, handheld electronic devices and other portable electronic devices are, by their very nature, at a greater risk of accidental exposure to moisture. It is not uncommon for users to carry sensitive equipment such as cellular telephones in a pocket when traveling outdoors. If a user receives a telephone call during a rainstorm, the user might use the cellular telephone before seeking shelter from the rain. Devices may also be left in environments in which condensation may lead to moisture infiltration.

Although devices can be made somewhat resistant to damage from small amounts of moisture, it is not feasible to completely waterproof most devices. For example, device ports may create potential locations through which moisture can reach the circuitry of an electronic device. Covering all of the ports in a device to prevent moisture damage might make the device too cumbersome to use. Moisture barrier structures may also add undesirable bulk and may make devices unsightly and expensive.

Because of these practical considerations, electronic devices are generally somewhat resistant to moisture exposure, but are not completely waterproof. Designing a device in this way maximizes user enjoyment and use of the device, but does not eliminate all risk of moisture-related damage.

Users are generally aware of the moisture sensitivity limits of modern electronic devices. For this reason, users take care to avoid submerging electronic devices in liquid. Even a careless user would not expect an electronic device such as a cellular telephone to be undamaged if fully immersed in liquid.

At the same time, manufacturers try to ensure that devices do not fail immediately upon exposure to trivial amounts of moisture. Overly sensitive devices would require frequent attention from customer service personnel.

Even though electronic devices are generally designed to be robust enough to withstand momentary exposure to trivial amounts of moisture, accidents can happen. For example, a user may drop a device into a body of water. When a device that has been damaged in this way stops working properly, the user may decide to return the device to the manufacturer for repair.

A large manufacturer of electronic devices can expect to receive returns from customers that have exposed their devices to excessive amounts of water. Often the damaged devices are dry when they are returned. To determine whether or not a device has been submerged in liquid, manufacturers often include moisture infiltration indicators (sometimes called "water dots" or "moisture indicators") in their devices. If the water dot in a returned device has not been activated, the manufacturer can conclude that damage to the device was caused by dropping the device onto a hard surface or another damaging event other than liquid exposure. If the water dot has been activated, the manufacturer can conclude that the device has failed due to excessive exposure to liquid.

The use of water dots to test for liquid exposure helps manufacturers to evaluate warranty claims and debug possible failure mechanisms. To avoid adversely affecting device aesthetics, it is often desirable to place water dots in discrete locations. At the same time, it may be desirable to place water dots in locations that are readily accessible by service personnel, so that a returned device does not need to be disassembled to examine the status of the water dot.

As an example, a water dot may be placed in a recessed portion of a device such as a device port. When a water dot is located in a device port, the water dot can be quickly examined by service personnel, but will not be unsightly to users.

Particularly when water dots are located in relatively exposed positions such as these, the water dots may become highly sensitive to moisture damage. This may make it impossible for service personnel to determine whether a device has failed from a small amount of moisture exposure of the type that would normally be covered by the manufacturer's warranty or whether the device has failed due to a complete submersion of the device in liquid.

It would therefore be desirable to be able to provide improved moisture indicator structures for electronic devices.

SUMMARY

An electronic device such as a portable electronic device may contain sensitive components. For example, an electronic device may contain printed circuit boards on which circuit components are mounted.

To avoid damage to the electronic device, a user should avoid any exposure to moisture. Sometimes, however, trivial amounts of moisture infiltrate an electronic device. A moisture indicator ("water dot") may be provided to monitor exposure of the electronic device to moisture.

To distinguish between situations in which an electronic device has been immersed in liquid or otherwise exposed to large amounts of moisture and situations in which the electronic device has been exposed to only a relatively small amount of moisture, the moisture indicator may be provided with a sealed edge. The sealed edge may reduce the sensitivity of the moisture indicator. The moisture indicator may have an unsealed edge through which moisture can enter the moisture indicator.

The moisture indicator may be mounted to a connector in an input-output port or other opening of the electronic device. This allows the status of the moisture indicator to be viewed without disassembling the electronic device. The moisture indicator may be mounted within the opening so that the unsealed edge is located within the interior of the electronic device. The sealed edge can be mounted in the end of the opening that is closer to the exterior of the device. Because the sealed edge blocks moisture, trivial amounts of moisture that reach the moisture indicator only along its sealed edge will not cause the moisture indicator to change color.

The moisture indicator may be provided with regions of different sensitivity. Different regions of the moisture indicator may be separated from each other using moisture-flow-altering structures. These structures may be formed by introducing moisture-blocking substances into a wicking layer at selected locations. Different wicking layer thicknesses and interposed layers of perforated moisture blocking material may also be used to provide the moisture indicator with regions of varying moisture sensitivity.

Further features of the invention, its nature and various advantages will be more apparent from the accompanying drawings and the following detailed description of the preferred embodiments.

DETAILED DESCRIPTION

Moisture infiltration indication structures may be provided for electronic devices.

The electronic devices may desktop computers, televisions, or other consumer electronics equipment. The electronic devices may also be portable electronic devices such as laptop computers or small portable computers of the type that are sometimes referred to as ultraportables. If desired, portable electronic devices may be somewhat smaller devices. Examples of smaller portable electronic devices include wrist-watch devices, pendant devices, headphone and earpiece devices, and other wearable and miniature devices. With one suitable arrangement, the portable electronic devices may be handheld electronic devices.

Electronic devices include circuitry. The circuitry typically includes electronic components such as integrated circuits and discrete devices such as capacitors, resistors, and inductors. Circuit components may be mounted on rigid and flexible printed circuit boards.

To determine whether an electronic device has been exposed to moisture, the electronic device may be provided with a moisture indicator. Moisture indicators, which are sometimes referred to as moisture intrusion indicators or water dots, may change color or otherwise alter their visual appearance when exposed to liquid. The state of a moisture indicator is therefore indicative of whether or not the electronic device has been handled properly. For example, a moisture indicator with an unchanged state indicates that a device has not been exposed to substantial amounts of moisture, whereas a moisture indicator with an activated state indicates that a device has been exposed to liquid.

To ensure that the moisture indicator is not overly sensitive, some or all of the edges of the moisture indicator may be sealed.

Figure 1:
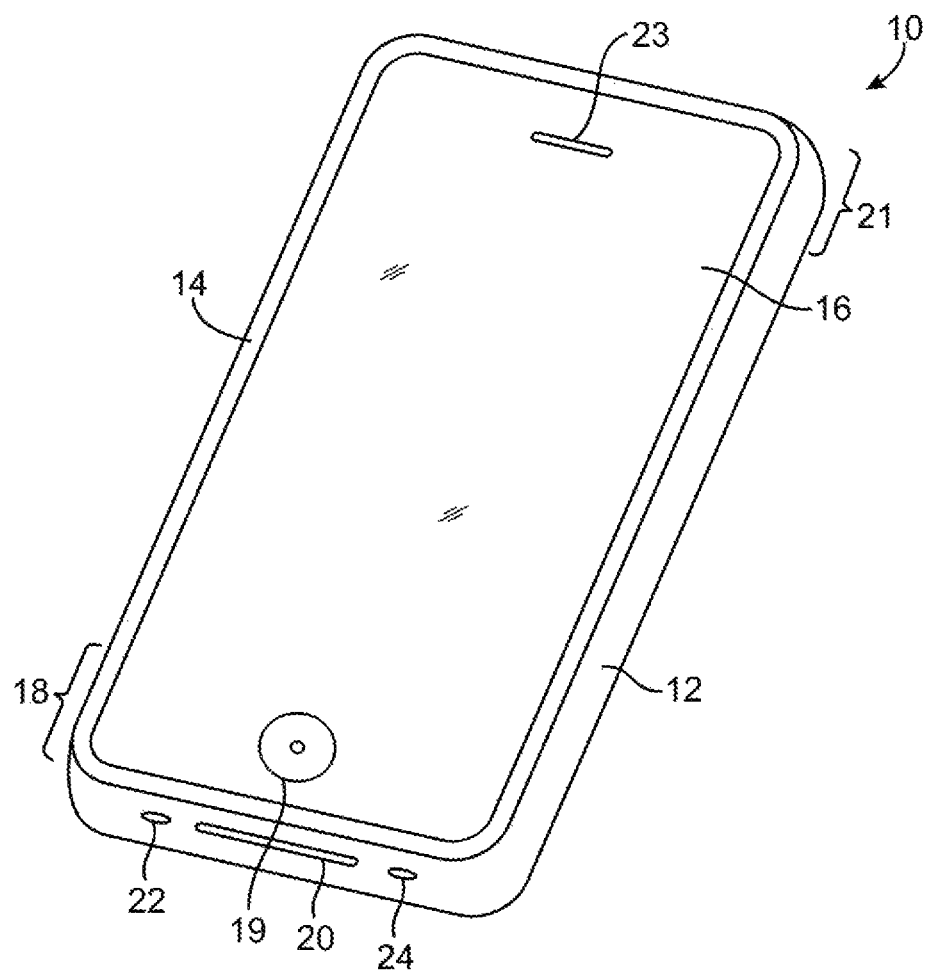
FIG. 1 is a perspective view of an illustrative electronic device that includes a moisture indicator in accordance with an embodiment of the present invention.

An illustrative electronic device is shown in accordance with an embodiment of the present invention is shown in FIG. 1. Device 10 of FIG. 1 may be, for example, a handheld electronic device that supports cellular telephone voice and data functions, global positioning system capabilities, local wireless communications capabilities (e.g., IEEE 802.11 and Bluetooth®), and other wireless functions. Device 10 may have storage and processing circuitry that allows device 10 to run code. The code may be used in implementing functions such as internet browsing functions, email and calendar functions, games, music player functionality, etc.

Device 10 may have housing 12. Antennas for handling wireless communications may be housed within housing 12 (as an example). Housing 12 may be formed of any suitable materials including, plastic, glass, ceramics, metal, other suitable materials, or a combination of these materials. Bezel 14 may be formed from a conductive material and may serve to hold a display or other device with a planar surface in place on device 10. Bezel 14 may also form an aesthetically pleasing trim around the edge of device 10.

Display 16 may be a liquid crystal display (LCD), an organic light emitting diode (OLED) display, or any other suitable display. The outermost surface of display 16 may be formed from one or more plastic or glass layers. If desired, touch screen functionality may be integrated into display 16 or may be provided using a separate touch pad device. An advantage of integrating a touch screen into display 16 to make display 16 touch sensitive is that this type of arrangement can save space and reduce visual clutter.

Display screen 16 (e.g., a touch screen) is merely one example of an input-output device that may be used with electronic device 10. If desired, electronic device 10 may have other input-output devices. For example, electronic device 10 may have user input control devices such as button 19 and input-output components such as port 20. Button 19 may be, for example, a menu button. Port 20 may contain a 30-pin data connector (as an example). Openings 22 and 24 may, if desired, form speaker and microphone ports. Speaker port 22 may be used when operating device 10 in speakerphone mode. Opening 23 may also form a speaker port. For example, speaker port 23 may serve as a telephone receiver that is placed adjacent to a user's ear during operation. In the example of FIG. 1, display screen 16 is shown as being mounted on the front face of handheld electronic device 10, but display screen 16 may, if desired, be mounted on the rear face of handheld electronic device 10, on a side of device 10, on a flip-up portion of device 10 that is attached to a main body portion of device 10 by a hinge (for example), or using any other suitable mounting arrangement.

A user of electronic device 10 may supply input commands using user input interface devices such as button 19 and touch screen 16. Suitable user input interface devices for electronic device 10 include buttons (e.g., alphanumeric keys, power on-off, power-on, power-off, and other specialized buttons, etc.), a touch pad, pointing stick, or other cursor control device, a microphone for supplying voice commands, or any other suitable interface for controlling device 10. Although shown schematically as being formed on the top face of electronic device 10 in the example of FIG. 1, buttons such as button 19 and other user input interface devices may generally be formed on any suitable portion of electronic device 10. For example, a button such as button 19 or other user interface control may be formed on the side of electronic device 10. Buttons and other user interface controls can also be located on the top face, rear face, or other portion of device 10. If desired, device 10 can be controlled remotely (e.g., using an infrared remote control, a radio-frequency remote control such as a Bluetooth® remote control, etc.).

Electronic device 10 may have ports such as port 20. Port 20, which may sometimes be referred to as a dock connector, 30-pin data port connector, input-output port, or bus connector, may be used as an input-output port (e.g., when connecting device 10 to a mating dock connected to a computer or other electronic device). Port 20 may contain pins for receiving data and power signals. Device 10 may also have audio and video jacks that allow device 10 to interface with external components. Typical ports include power pins to recharge a battery within device 10 or to operate device 10 from a direct current (DC) power supply, data pins to exchange data with external components such as a personal computer or peripheral, audio-visual jacks to drive headphones, a monitor, or other external audio-video equipment, a subscriber identity module (SIM) card port to authorize cellular telephone service, a memory card slot, etc. The functions of some or all of these devices and the internal circuitry of electronic device 10 can be controlled using input interface devices such as touch screen display 16.

Device 10 may include one or more printed circuit boards. The printed circuit boards of device 10 may be formed from rigid printed circuit board material (e.g., fiberglass-filled epoxy). Flexible printed circuit boards ("flex circuits") may be formed using sheets of flexible polymers such as polyimide (as an example). Rigid and flexible printed circuit boards may be used to mount integrated circuits such as storage devices, processors, application specific integrated circuits, radio-frequency transceivers and other wireless circuitry, and other circuits. The wireless circuitry may include antennas. Examples of locations in which antennas may be located in device 10 include region 18 at the lower end of device 10 and region 21 at the upper end of device 10.

The circuitry within device 10 is generally not designed to be completely waterproof. As a result, excessive moisture may potentially damage device 10. Damage due to extreme moisture exposure such as exposure when device 10 is immersed in liquid is generally due to mishandling. For example, a user may accidentally drop device 10 into a body of water. Device 10 is not designed to withstand this type of abuse and will therefore probably fail. If a user of device 10 seeks warranty coverage, it would be helpful to determine whether device 10 has been abused by submersion in liquid.

Other types of damage may arise when device 10 is exposed to more modest amounts of moisture. For example, a small amount of perspiration may enter device 10 in the vicinity of port 20 when a user is working out at the gym. As another example, a user may place device 10 in a cup holder in a car in which a small amount of condensation from a cold drink has collected. This small amount of water might also enter device 10 in the vicinity of port 20.

Because device 10 is not designed to be waterproof, it is conceivable that these relatively small amounts of moisture may adversely affect proper device operation. It may be desirable to provide a user with warranty coverage in such circumstances, because the user did not abuse the device.

To distinguish between relatively large amounts of moisture infiltration and relatively small amounts of moisture infiltration in device 10, moisture indicator structures may be provided in device 10 that can help measure different amounts of moisture exposure. Moisture indicators such as these may be located in any suitable portion of device 10. For example, moisture indicators can be provided in the interior of device 10 adjacent to a printed circuit board or other sensitive circuitry.

In some circumstances, service personnel may want to quickly ascertain the moisture exposure status of a device without opening up the device to inspect an internally mounted moisture indicator. To accommodate this type of need and to ensure that moisture indicators are provided in portions of device 10 in which moisture is likely to intrude, device 10 may be provided with one or more moisture indicators in the vicinity of device ports. For example, device 10 may be provided with a moisture indicator in port 20. By placing the moisture indicator in a portion of device 10 that is visible from the exterior of device 10, the need to open up device 10 to check the status of the moisture indicator can be avoided. Other mounting arrangements for moisture indicators may be used if desired. A configuration in which a moisture indicator is mounted within port 20 in a location that is visible from the exterior of device 10 by service personnel is sometimes described herein as an example.

A moisture indicator is typically constructed from layers of different materials. For example, a moisture indicator may have a paper layer or other suitable wicking layer on which a dye layer is formed. The dye may be formed from any suitable colored substance and may sometimes be referred to as ink or pigment. When the wicking layer is exposed to moisture, the dye bleeds into the wicking layer and changes its appearance. The dye may be, for example, a red dye. The wicking layer may be, for example, white paper.

Figure 2A:
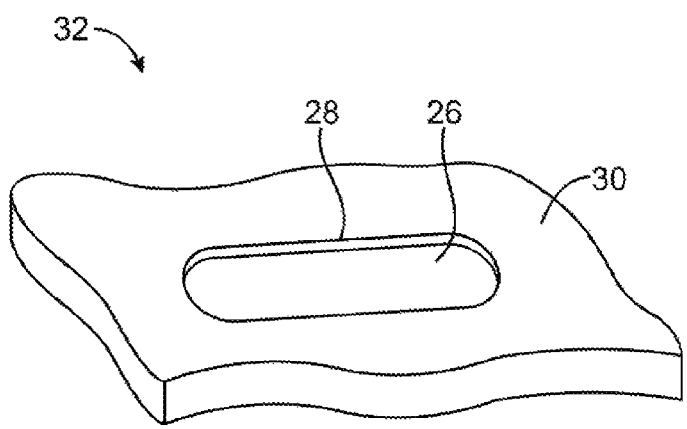
FIG. 2A shows how a moisture indicator may have a first appearance when it has not been exposed to moisture in accordance with an embodiment of the present invention.
Figure 2B:
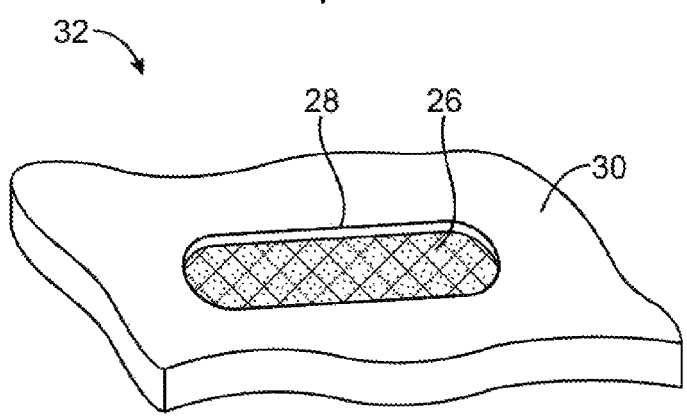
FIG. 2B shows how a moisture indicator of the type shown in FIG. 2A may have a second appearance when it has been exposed to moisture in accordance with an embodiment of the present invention.

The behavior of a moisture indicator of this type is illustrated in FIGS. 2A and 2B. As shown in FIG. 2A, Moisture indicator 32 may have a visible surface 26. Surface 26 may be, for example, a wicking layer that has been optionally covered with a transparent moisture barrier layer. In the example of FIG. 2A, moisture indicator 32 has been mounted under hole 28 in member 30. Member 30 may be part of a connector member in port 20 or may be any other suitable structural portion of device 10.

Initially, moisture indicator 32 is unexposed to moisture. When moisture indicator becomes wet, however, the dye layer will bleed into the wicking layer. The resulting change in appearance of surface 26 (e.g., from white to red) is illustrated in FIG. 2B.

Figure 3:
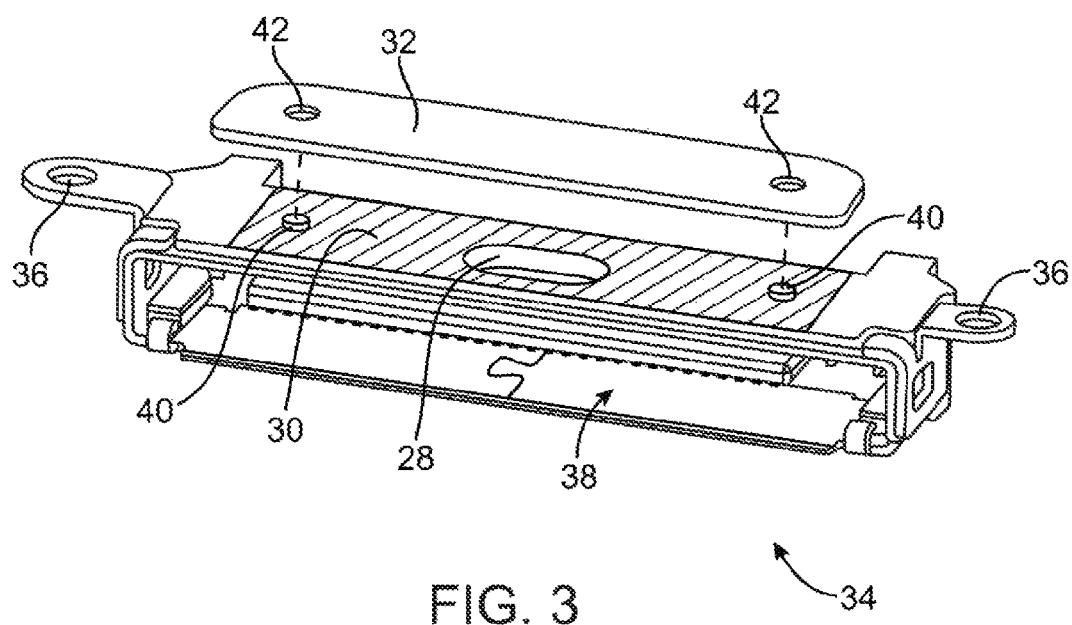
FIG. 3 is a perspective view of a connector structure and an associated moisture indicator of the type that may be used in an electronic device such as the electronic device of FIG. 1 in accordance with an embodiment of the present invention.

Moisture indicator 32 may be mounted in any suitable portion of device 10. An illustrative mounting arrangement that may be used in which moisture indicator 32 is mounted on a connector associated with port 20 is shown in FIG. 3. As shown in FIG. 3, connector 34 may have tab structures 36 that are used in securing connector 34 to device 10 in port 20. Connector 34 may be, for example, a 30-pin connector. When it is desired to connect a 30-pin cable to device 10, the head of the 30-pin connector may be inserted into connector 34 in opening 38.

Member 30 of connector 34 may have registration pins 40. Moisture indicator 32 may be formed from a series of planar layers. As shown in FIG. 3, holes 42 may be formed in the layers of moisture indicator 32 that match registration pins 40. This may help to align moisture indicator to member 30 of connector 34. Adhesive or other suitable fastening mechanisms may be used to secure moisture indicator 32 to member 30. With the arrangement shown in FIG. 3, surface 26 (FIGS. 2A and 2B) of moisture indicator 32 faces downwards through hole 28 in member 30. Service personnel can therefore examine the status of moisture indicator 32 by looking into hole 38 of connector 34 when connector 34 is mounted in the lower portion of device 10 to form port 20 (FIG. 1).

Figure 4:
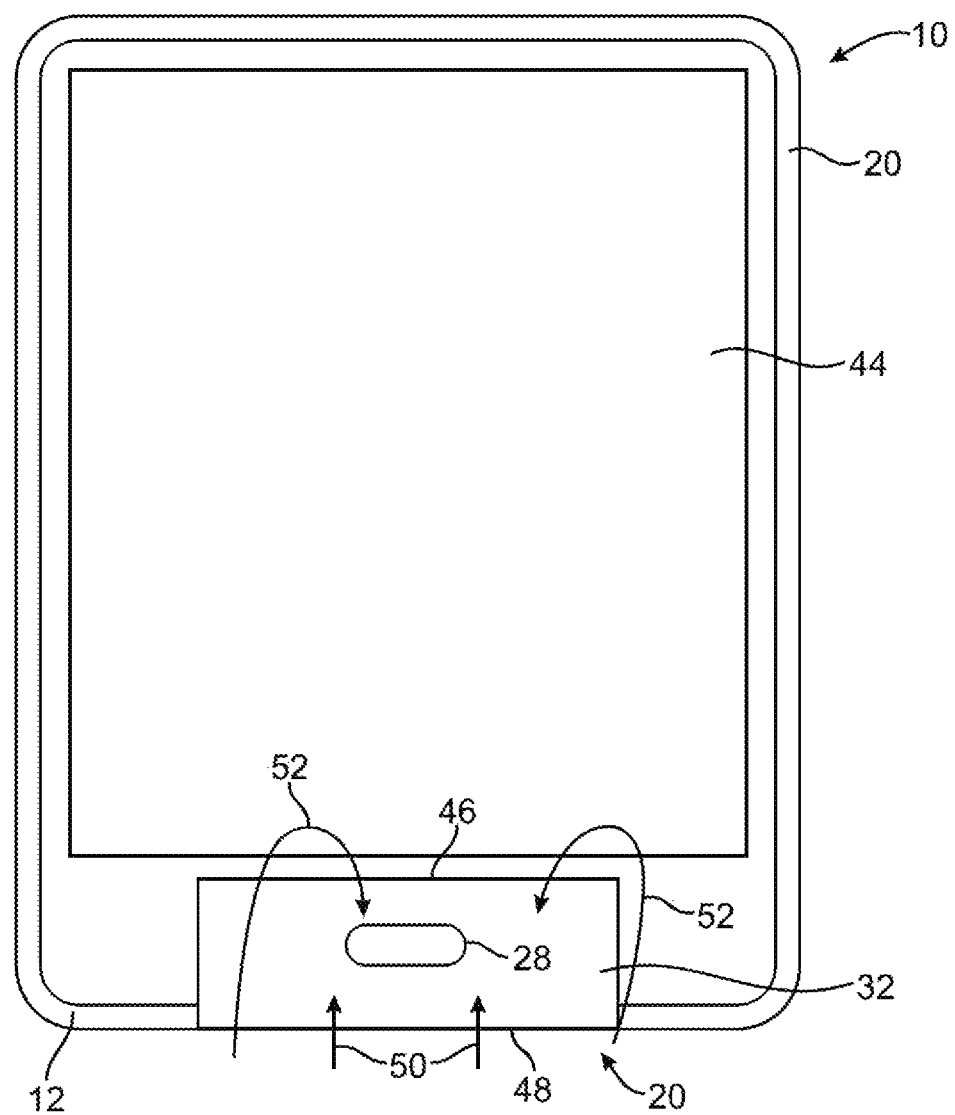
FIG. 4 is a diagram showing how a moisture indicator may be located at the lower end of an electronic device in accordance with an embodiment of the present invention.

FIG. 4 shows potential pathways for moisture entering device 10. As shown in FIG. 4, device 10 may contain sensitive components 44 such as printed circuit board structures to which circuitry is mounted. Moisture indicator 32 may be mounted on a connector such as connector 34 of FIG. 2 in port 20 so that the status of the moisture indicator can be visually examined through hole 28. When located as shown in FIG. 4, moisture can reach moisture indicator 32 along lower edge 48 following paths 50 or can reach moisture indicator 32 along upper edge 46 along paths such as path 52.

Proper operation of moisture indicator 32 can be achieved by adjusting its sensitivity so that trivial amounts of moisture exposure are distinguishable from excessive amounts of moisture exposure. With one suitable arrangement, the upper and lower planar surfaces of moisture indicator 32 may be covered by moisture barrier layers and some of the edges of the moisture barrier layers may be sealed to prevent moisture intrusion. For example, lower edge 48 may be sealed to prevent moisture from entering moisture indicator 32 along paths 50, whereas upper edge 46 may remain unsealed to allow moisture to enter moisture indicator 32 along paths 52. Small amounts of moisture may sometimes enter the device 10 along paths 50, so it can be helpful to reduce the sensitivity of moisture indicator 32 to moisture exposure of this type. At the same time, moisture that has reached moisture indicator 32 after traveling along paths 52 is likely to have damaged sensitive components 44, so it is helpful for this type of moisture exposure to activate moisture indicator 32.

Figure 5:
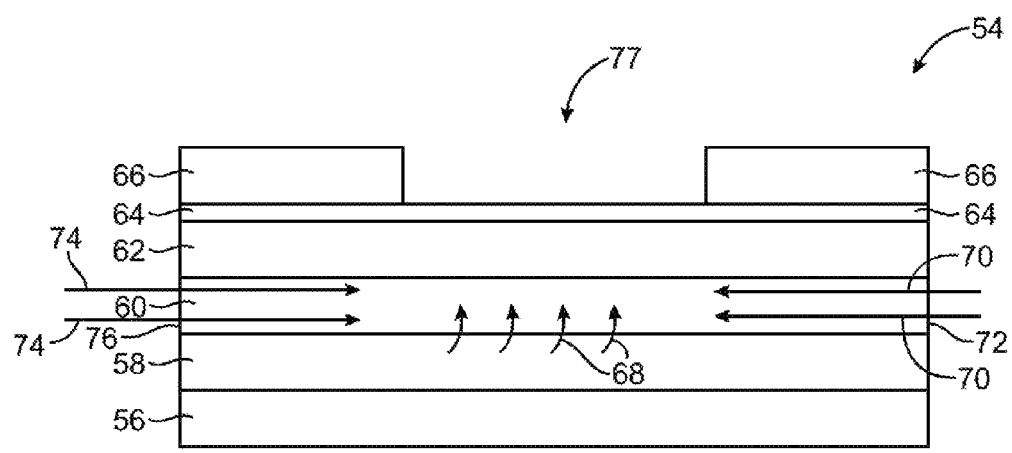
FIG. 5 is a cross-sectional side view of a conventional moisture indicator.

A cross-sectional side view of a conventional moisture indicator is shown in FIG. 5. As shown in FIG. 5, moisture indicator 54 may have white paper layer 60 and red dye layer 58. Moisture indicator 54 may be mounted to the lower side of member 66 using adhesive 64, so that visual inspection of the upper surface of moisture indicator 54 may be made in direction 77 through a hole in member 66. The upper and lower planar surfaces of moisture indicator 54 may be sealed using lower moisture barrier layer 56 and upper moisture barrier layer 62. Moisture barrier layers 56 and 62 are formed from polyethylene terephthalate (PET). Upper moisture barrier layer 62 is clear, so that the color of wicking layer 60 is visible from direction 77.

The edges of conventional moisture indicators such as moisture indicator 54 of FIG. 5 are not sealed. This allows moisture to enter wicking layer 60 from any edge of moisture indicator 54 that is exposed to moisture. For example, moisture may enter layer 60 along unsealed edge 72 following paths 70 and may enter layer 60 along unsealed edge 76 following paths 74. Once moisture has entered wicking layer 60, dye from layer 58 may bleed into wicking layer 60 along paths 68. The resulting presence of dye in layer 60 may be observed visually from direction 77.

To properly tailor moisture indicator sensitivity, some of edge portions of a moisture indicator may be sealed. An example is shown in the cross-section of FIG. 6.

Figure 6:
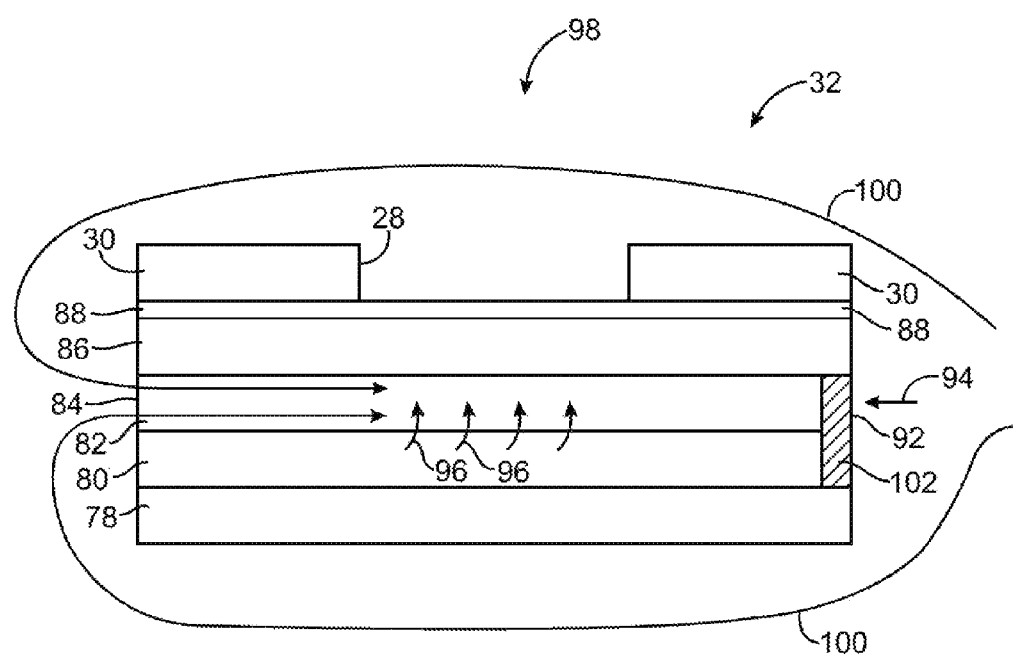
FIG. 6 is a cross-sectional side view of a moisture indicator in accordance with an embodiment of the present invention.

As shown in FIG. 6, moisture indicator 32 may have wicking layer 82 and dye layer 80. Wicking layer 82 may be formed from white paper or other suitable moisture-permeable material. Dye layer 80 may be formed from a red water-soluble dye or other suitable substance that bleeds into wicking layer 82 upon exposure to moisture.

Moisture indicator 32 may have moisture barrier layers such as upper moisture barrier layer 86 and lower moisture barrier layer 78 that cover the wicking layer 82 and dye layer 80. Layers 78 and 86 may be formed from a moisture-repellent (impermeable) material such as polyethylene terephthalate (PET). Upper moisture barrier layer 86 may be transparent, so that the color of wicking layer 82 is visible from direction 98.

Adhesive 88 or other suitable fastening mechanisms may be used to attach moisture indicator 32 to member 30. Member 30 may be, for example, part of connector 34 of FIG. 4 and may be located in a portion of device 10 where moisture indicator 32 is visible through hole 28 when viewed from direction 98.

Upper moisture barrier 86 and lower moisture barrier 78 may be sealed using an impermeable (moisture-proof) material such as paint, adhesive, etc. As shown in FIG. 6, impermeable material 102 may be placed along edge 92 of moisture indicator 32 so that edge 92 is sealed to moisture. With this type of configuration, moisture that approaches moisture indicator 32 along path 94 will be blocked by the sealed moisture barrier layers along edge 92, but moisture that approaches moisture indicator 32 along paths 100 will be able to enter wicking layer 82 through unsealed edge 84. Once this moisture enters moisture indicator 32, dye in layer 80 may bleed into wicking layer 82 along paths 96 to visually indicate that moisture has been detected.

By sealing edge regions of moisture indicator 32, moisture indicator 32 can be desensitized. As a result, the presence of trivial amounts of moisture will not result in a positive moisture reading. If desired, sealed edges such as edge 92 may be located adjacent to the entrance of an opening in device 10, where small amounts of moisture intrusion are most likely, whereas the unsealed portions of moisture indicator 32 such as unsealed edge 84 can be located further into the interior of device 10. For example, edge 92 may be located along the lowermost edge of connector 34 in port 20 near the surface of device 10, whereas edge 84 may be located along the uppermost edge of connector 34 (i.e., several millimeters or more inside device 10).

Figure 7:
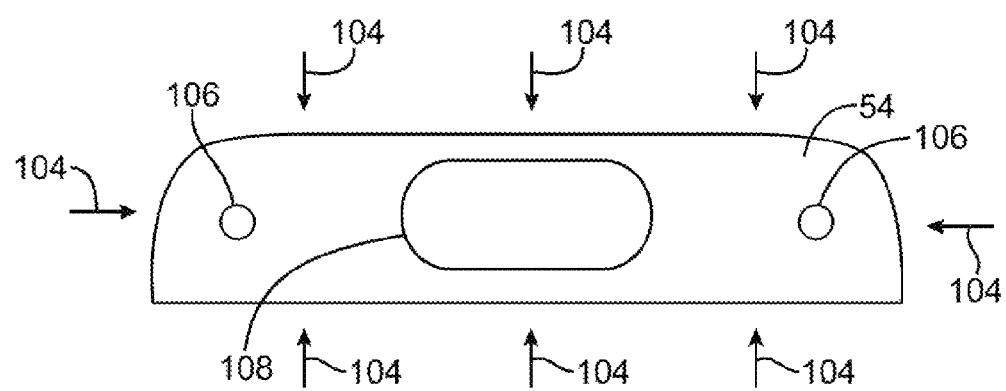
FIG. 7 is a top view of a conventional moisture indicator showing directions from which moisture may enter the moisture indicator.

Any suitable edges of a moisture indicator may be sealed. A top view of a conventional moisture indicator 54 is shown in FIG. 7. As shown in FIG. 7, moisture indicator 54 may have registration holes 106 and may have a central portion 108 that is viewable through a hole in a connector such as connector 34 of FIG. 3. All of the edges (top, bottom, left, and right) of moisture indicator 54 of FIG. 7 are unsealed edges such as edges 76 and 72 of FIG. 5. With this type of arrangement, moisture can enter moisture indicator 54 of FIG. 7 from any direction 104.

Figure 8:
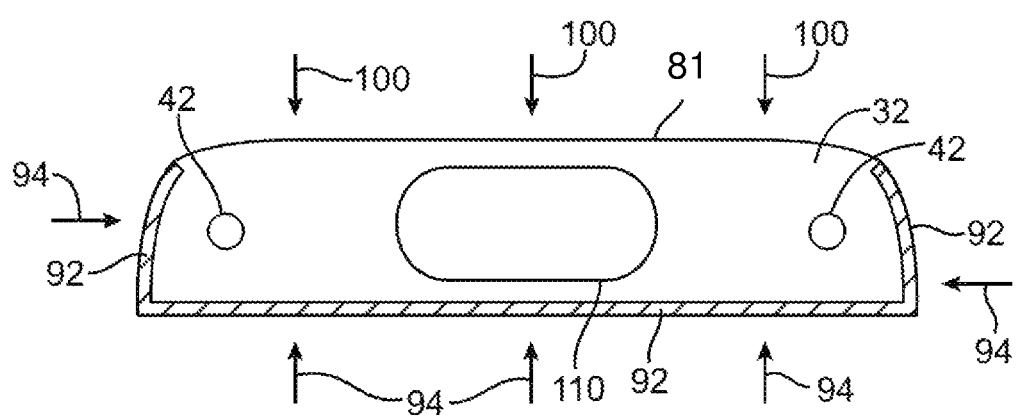
FIG. 8 is a top view of a moisture indicator showing directions from which moisture may enter the moisture indicator and directions in which moisture entry is blocked in accordance with an embodiment of the present invention.

A moisture indicator with sealed edges is shown in FIG. 8. As shown in FIG. 8, moisture indicator 32 may have a central region 110 that can be aligned with hole 28 in member 30 (FIG. 3). Moisture indicator 32 of FIG. 8 may have a cross-section of the type shown in FIG. 6. Upper and lower barrier layers may be sealed along edges 92 and may be unsealed along edge 81. This prevents moisture from entering moisture indicator 32 along paths 94, but allows moisture to enter the wicking layer of moisture indicator 32 along paths 100. By orienting moisture indicator 32 of FIG. 8 so that lower sealed edge 92 of moisture indicator 32 is aligned with the lowermost edge of connector 34 (FIG. 3) in port 20 (FIG. 1), moisture indicator 32 can be prevented from being overly sensitive. Small amounts of moisture that come into contact with the portions of moisture indicator 32 along lower edge 92 will not cause moisture indicator 32 to change state. However, larger amounts of moisture, such as moisture resulting from immersion of device 10 in liquid, can enter moisture indicator 32 along unsealed edge 81 within the interior of device 10.

Figure 9:
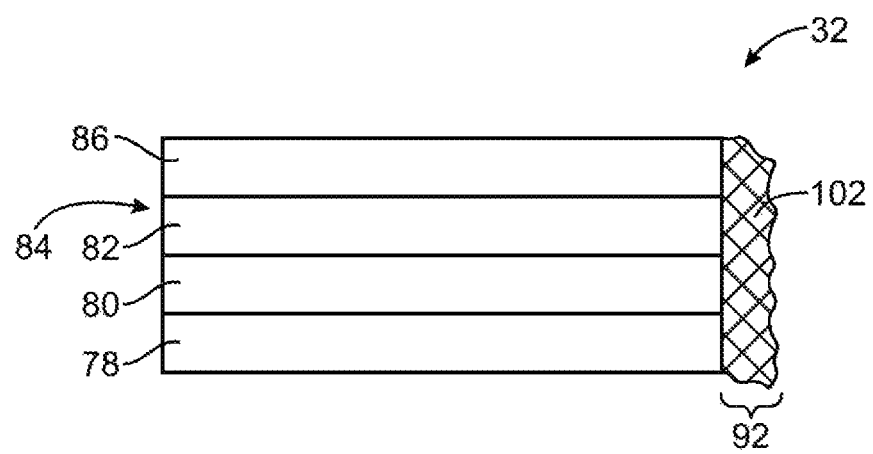
FIG. 9 is a cross-sectional side view of a moisture indicator showing how moisture can be blocked from entering the moisture indicator using an impermeable substance to seal an edge of the moisture indicator in accordance with an embodiment of the present invention.

Any suitable technique may be used for sealing edge portions such as edge portions 92. With the illustrative arrangement of FIG. 9, an impermeable seal has been created between upper moisture barrier layer 86 and lower moisture barrier layer 78 by coating edge 92 with paint, adhesive, other substances that are liquid when applied but that transform into solids when cured, or other impermeable substances 102.

Figure 10:
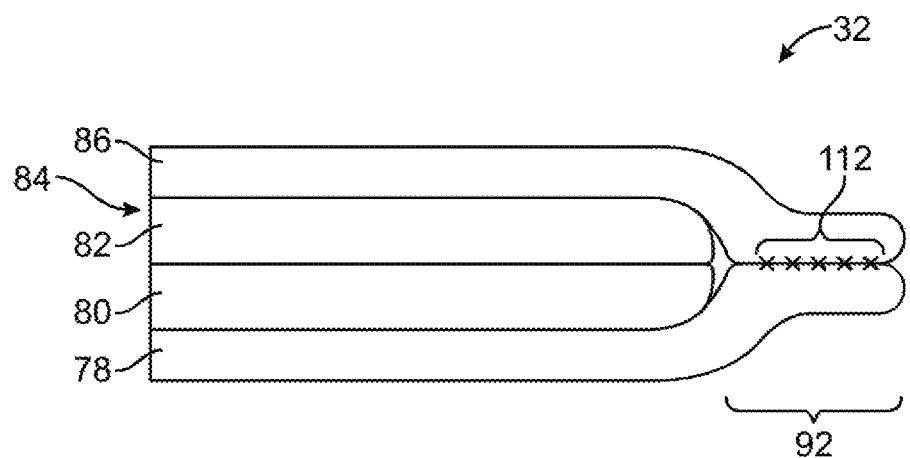
FIG. 10 is a cross-sectional side view of a moisture indicator showing how moisture can be blocked from entering the moisture indicator by joining upper and lower moisture barrier layers along an edge of the moisture indicator in accordance with an embodiment of the present invention.

Another possible arrangement is shown in FIG. 10. With the illustrative configuration of FIG. 10, upper moisture barrier layer 86 and lower moisture barrier layer 78 are joined along region 112 to ensure that edge 92 of moisture indicator 32 is sealed. Moisture barrier layer 86 and moisture barrier layer 78 may be sealed in region 112 using heat treatment (e.g., to melt or soften layers 86 and 78), using adhesive, using combinations of pressure, heat, and adhesive, using clips or other connective structures, or using any other suitable sealing techniques.

Figure 11:
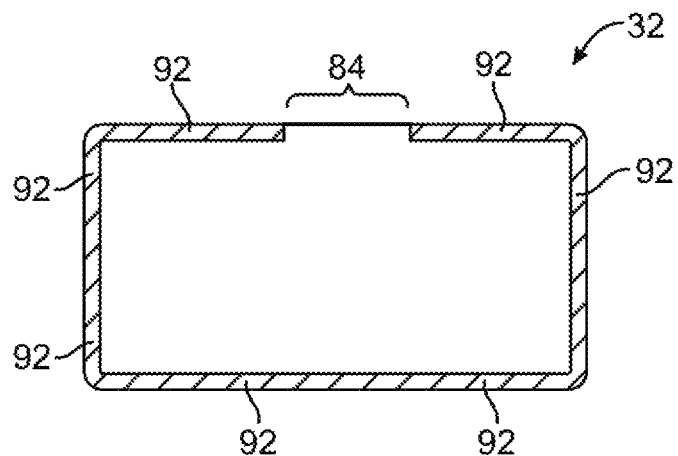
FIG. 11 is a top view of an illustrative moisture barrier showing how a single opening may be formed in the otherwise sealed edge of a moisture indicator in accordance with an embodiment of the present invention.
Figure 12:
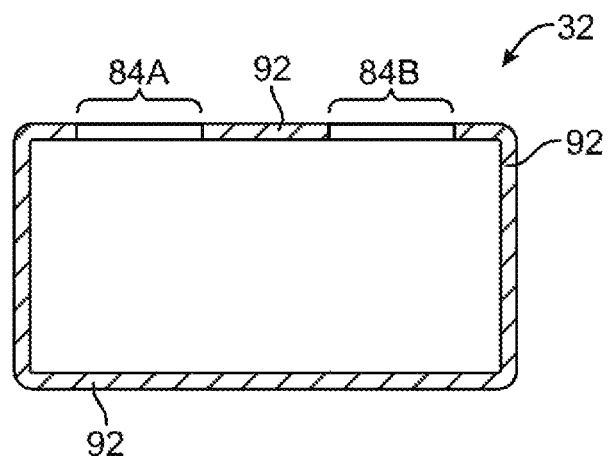
FIG. 12 is a top view of an illustrative moisture indicator showing how multiple openings may be formed in the sealed edge of a moisture indicator in accordance with an embodiment of the present invention.

One or more edge portions of moisture indicator 32 may be left unsealed. As shown in FIG. 11, unblocked edge 84 of moisture indicator 32 may occupy only a fraction of the total upper edge of the moisture sensor, whereas all remaining edges 92 may be sealed (as an example). FIG. 12 shows an illustrative configuration in which multiple edge segments 84A and 84B are unsealed and the remaining edge portions 92 are sealed.

By adjusting the sensitivity of moisture indicator 32 to moisture exposure, moisture indicator 32 can be configured to provide a desired amount of moisture intrusion status information. For example, moisture indicator 32 can be configured to alert service personnel to extreme exposures to moisture, but not trivial exposures to moisture (as an example).

If desired, moisture indicator 32 may be provided with multiple regions, each of which changes state (e.g., from white to red) under different moisture exposure conditions. The thickness of wicking layer 82 can influence the sensitivity of moisture indicator 32 to moisture, so one illustrative configuration for providing moisture indicator 32 with regions of varying moisture sensitivity involves providing moisture indicator 32 with regions of different wicking layer thickness. The movement of moisture through wicking layer 82 can also be influenced by introducing foreign substances into wicking layer 82. For example, the flow of moisture can be influenced by incorporating an impermeable substance such as wax, paint, or adhesive into parts of wicking layer 82. Additional configurations are also possible (e.g., using wicking layer materials with different properties, using blocking layers with holes or other shapes, using combinations of these arrangements, or other suitable configurations).

Figure 13:
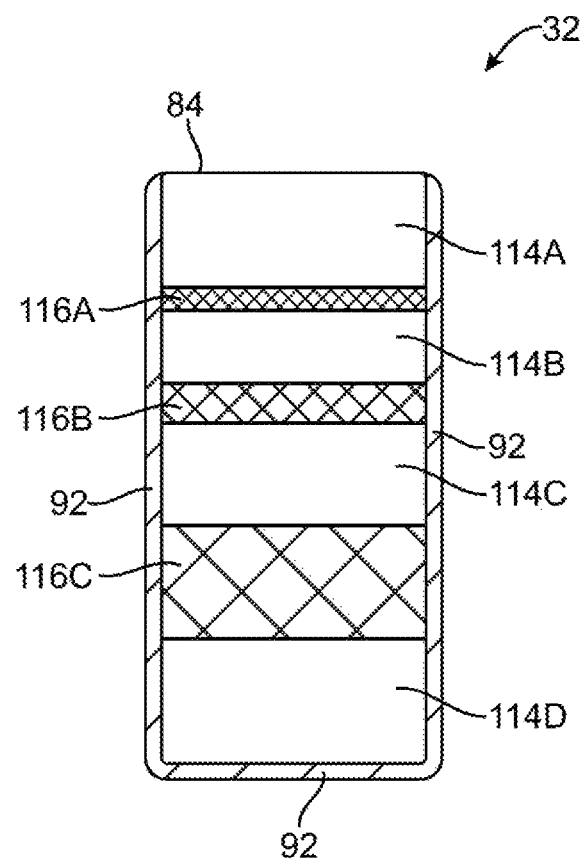
FIG. 13 is a top view of an illustrative multi-region moisture indicator in accordance with an embodiment of the present invention.

An illustrative moisture indicator with multiple regions is shown in FIG. 13. In the example of FIG. 13, moisture indicator 32 has an upper edge 84 that is unsealed and has right, left, and lower edges 92 that are sealed (i.e., that have moisture barrier layers that are connected together to prevent moisture intrusion).

Moisture indicator 32 of FIG. 13 has four regions 114A, 114B, 114C, and 114D that are separated by three regions 116A, 116B, and 116C. Regions 114A, 114B, 114C, and 114D may be, for example, regions of wicking material that are coated with transparent moisture barrier layer material. Regions 116A, 116B, and 116C may be portions of moisture indicator 32 that have modified properties (e.g., through the introduction of moisture blocking materials such as wax into the wicking layer, through the thickening or thinning of the wicking layer, etc.).

With one suitable arrangement, which is sometimes described herein as an example, the presence of regions 116A, 116B, and 116C may serve to impede moisture intrusion. This can help make the appearance of moisture indicator 32 more distinct and easier to interpret under a variety of moisture exposure conditions. For example, the presence of regions 116A, 116B, and 116C may lead to an overall structure in which region 114A is most sensitive to moisture, region 114B is less sensitive to moisture intrusion than region 114A, region 114C is less sensitive to moisture intrusion than region 114B, and region 114D is the least sensitive region in moisture indicator 32. In the absence of structures 116A, 116B, and 116C, it might be difficult to distinguish between relatively small amounts of moisture exposure and relatively large amounts of moisture exposure.

When an arrangement of the type shown in FIG. 13 is used, however, exposure to an extremely large amount of liquid may cause regions 114A, 114B, 114C, and 114D to all change from white to red, whereas exposure to a small amount of liquid might cause only regions 114A and 114B to turn red (as an example). The sizes of regions 116A, 116B, and 116C may be identical (to provide moisture indicator 32 with a linear response characteristic) or may be progressively larger or smaller (e.g., to provide moisture indicator 32 with a logarithmic or exponential response).

Figure 14:
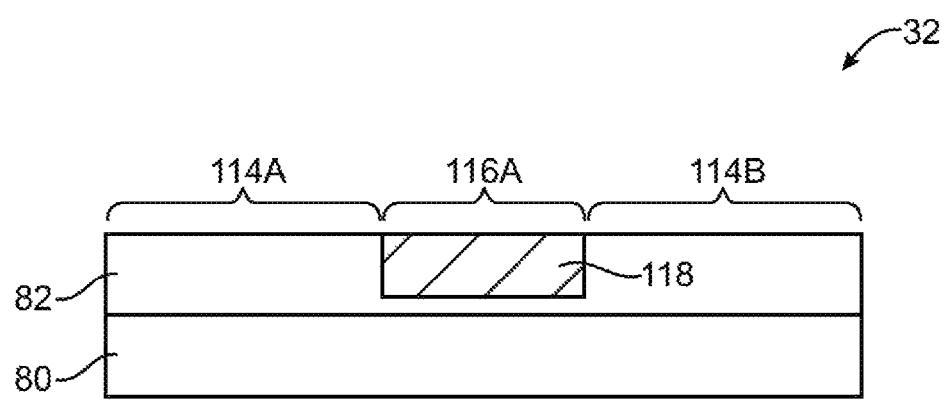
FIGS. 14 and 15 are cross-sectional side views of an illustrative moisture indicator structure showing how a moisture indicator wicking layer may be provided with portions with different wicking properties in accordance with an embodiment of the present invention.

One way in which to selectively impede the flow of moisture through moisture indicator 32 so that the individual states of regions such as regions 114A, 114B, 114C, and 114D can distinctly represent different amounts of moisture exposure involves introducing foreign substances into wicking layer 82. This type of configuration is shown in FIG. 14. As shown in FIG. 14, wicking layer 82 may have a first portion under region 114A and a second portion under region 114B between which (in region 116A) foreign substance 118 is introduced. The foreign substance in region 116A may be, for example, a material such as wax (e.g., an impermeable material) that is resistant to the wicking of moisture. The presence of substance 118 impedes moisture flow from region 114A to 114B and therefore makes region 114A more sensitive to moisture events than region 114B. Because structures such as the structure in region 116A of FIG. 14 serve to impede the flow of moisture through wicking layer 82, structures such as structure 116A may sometimes be referred to as moisture flow impeding structures of moisture flow altering structures.

Figure 15:
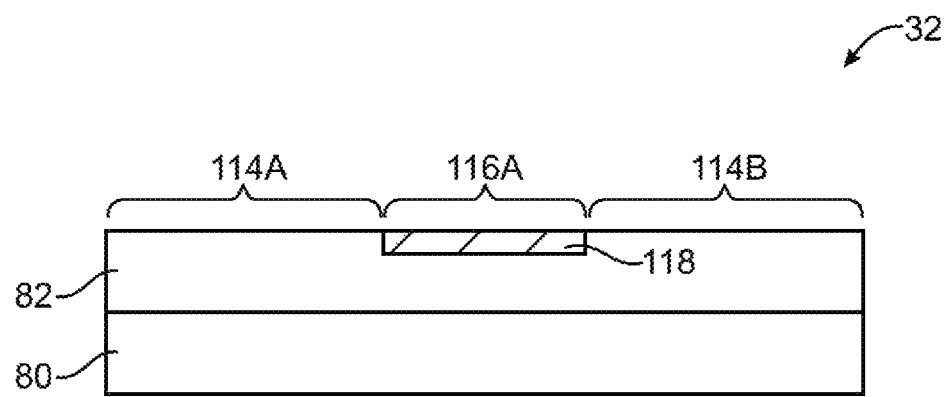

When substance 118 is impermeable, it may be desirable to limit the penetration depth of substance 118 into wicking layer 82. A cross-sectional view of a portion of an illustrative moisture indicator 32 in which the depth of substance 118 is relatively shallow is shown in FIG. 15 as an example.

Figure 16:
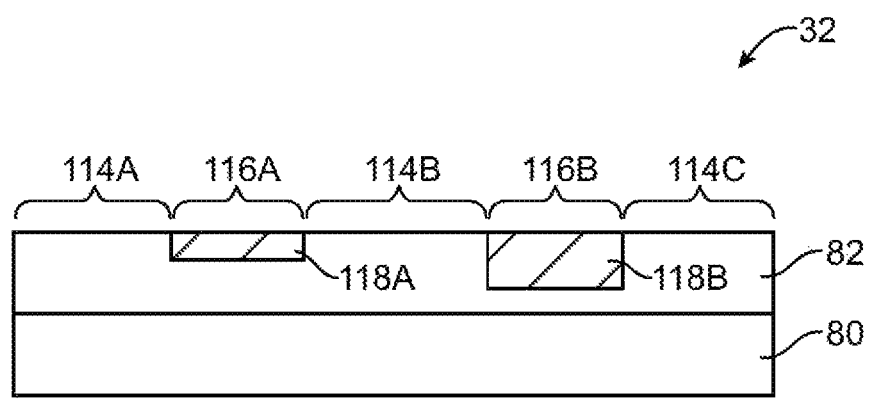
FIG. 16 is a cross-sectional side view of an illustrative moisture indicator structure showing how wax or other substances may be placed in two or more portions of a wicking layer in accordance with an embodiment of the present invention.

As shown in FIG. 16, a given moisture indicator may have multiple regions such as regions 116A and 116B with different depths (in addition to or instead of having different widths). With the illustrative structures of FIG. 16, regions 114A and 114B are separated by a moisture flow impeding structure that is relatively shallow (structure 118A or moisture flow impeding region 116A), whereas regions 114B and 114C are separated by a moisture flow impeding structure that is relatively deep (structure 118B in moisture flow impeding region 116B). In this type of arrangement, the deep shape of the structure in region 116B will ensure that region 114C will only change state when moisture indicator 32 has been exposed to a relatively large amount of moisture. The moisture flow altering structure in region 116A will help to distinguish the moisture level at which regions 114A and 114B change state (i.e., the structures of region 116A will introduce a threshold that ensures that region 114B will only turn red if a significantly larger amount of moisture is detected than the amount of moisture needed to turn region 114A red.

Figure 17:
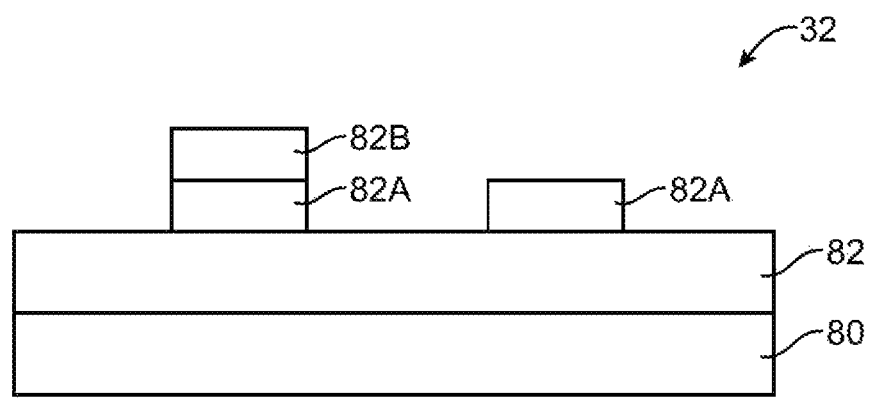
FIG. 17 is a cross-sectional side view of an illustrative moisture indicator structure showing how one or more regions of a wicking layer may be selectively thickened in accordance with an embodiment of the present invention.

In the example of FIG. 17, the moisture wicking behavior of layer 82 has been selectively altered in certain regions by adding one or two additional wicking layers (i.e., layer 82A and layer 82B). In regions where more wicking material is present, a relatively larger amount of moisture may need to be present to indicate the presence of moisture. The thicker wicking layer regions may also exhibit altered lateral moisture flow characteristics (e.g., as with regions 116A and 116B of FIG. 16 as an example).

Figure 18:
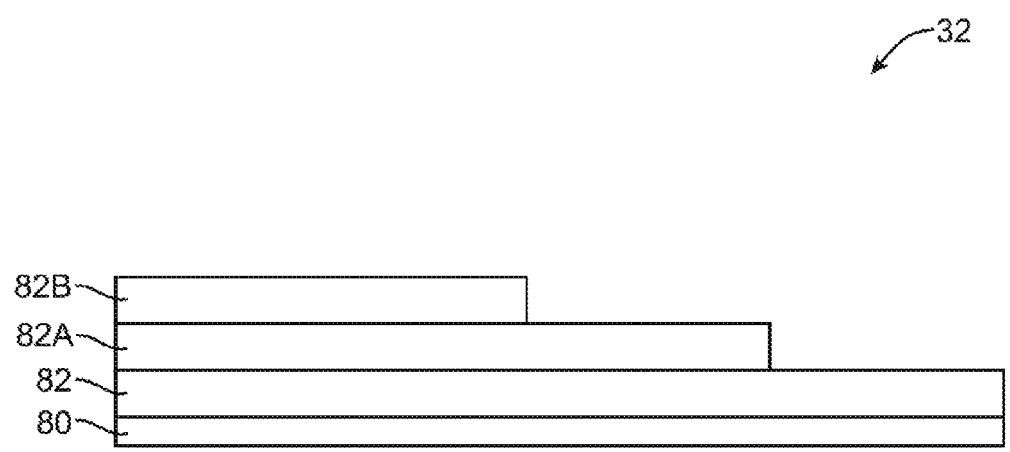
FIG. 18 is a cross-sectional side view of an illustrative moisture indicator structure showing how a wicking layer structure may be selectively thickened using multiple layers of wicking material in certain areas in accordance with an embodiment of the present invention.

The cross-sectional side view of FIG. 18 shows how moisture indicator 32 may be provided with several overlapping layers of wicking material. In the example of FIG. 18, wicking layer 82 covers all of the planar surface of moisture indicator 32, wicking layer 82A covers a portion of layer 82, and wicking layer 82B covers a portion of layer 82A. This type of structure makes moisture indicator 32 less sensitive in some regions (e.g., under the thicker wicking layer regions) than in other regions. If a small amount of moisture comes into contact with moisture indicator 32, only the thin regions of wicking material may exhibit bleed-through from the underlying dye layer. If moisture indicator 32 of FIG. 18 is exposed to relatively large amounts of moisture, all regions of the moisture indicator would change to red to indicate the occurrence of a moisture exposure event. Intermediate levels of moisture exposure might only change the exposed portions of layers 82 and 82A to a red color. As with the other multi-region moisture indicator arrangements, the use of multiple regions in a sensor of the type shown in FIG. 18 may make it easier for service personnel to accurately distinguish between different levels of moisture exposure. Service personnel may, for example, simply count the number of moisture indicator regions that have changed their color from white to red to determine the amount of moisture to which device 10 was exposed.

Figure 19:
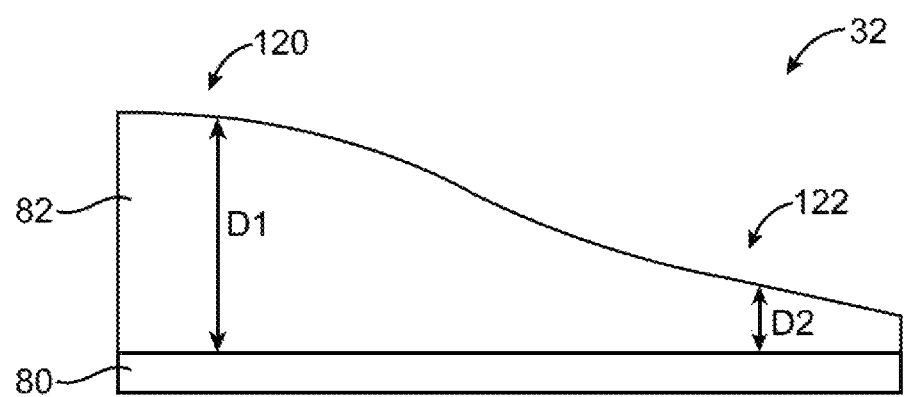
FIG. 19 is a cross-sectional side view of an illustrative moisture indicator structure showing how a wicking layer structure may be progressively thickened to spatially alter moisture indicator sensitivity in accordance with an embodiment of the present invention.

As shown in FIG. 19, moisture indicator 32 may be provided with a wicking layer that has smooth changes in thickness. In the FIG. 19 example, wicking layer 82 has a thickness D1 in region 120 and a thickness D2 in region 122. Because thickness D1 is greater than thickness D2, relatively more moisture exposure may be required to cause the color of layer 82 to change in region 120 than in region 122.

Figure 20:
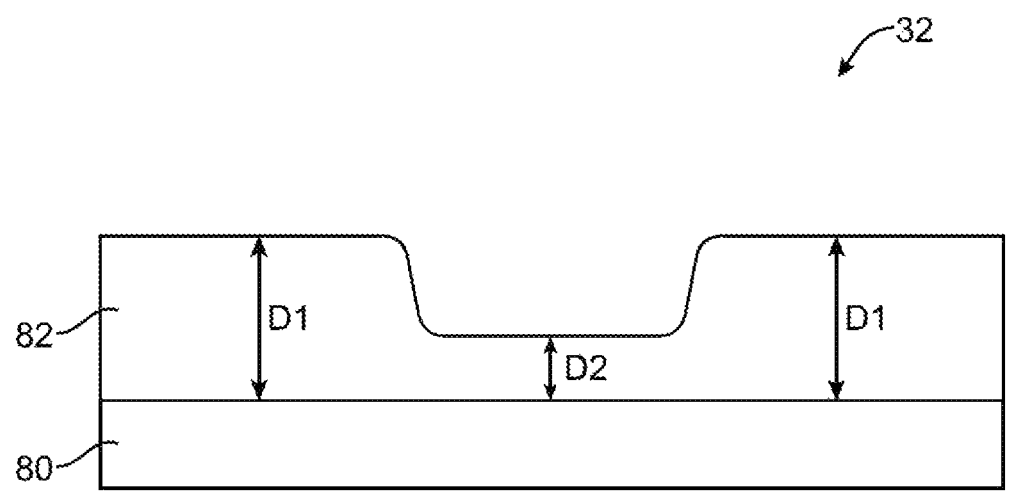
FIG. 20 is a cross-sectional side view of an illustrative moisture indicator structure showing how a wicking layer structure may be selectively thinned to spatially alter moisture indicator sensitivity in accordance with an embodiment of the present invention.

FIG. 20 shows a cross-sectional view of an illustrative moisture indicator 32 in which wicking layer 82 has been selectively thinned. This type of arrangement may be used to locally sensitize moisture indicator 32 or to create moisture flow altering structures.

If desired, layers of material such as impermeable material or material with different moisture flow properties than wicking layer 82 may be interposed between wicking layer 82 and dye layer 80. For example, a moisture barrier layer (e.g., a PET layer with perforations or other openings) may be interposed between dye layer 80 and wicking layer 82.

Figure 21:
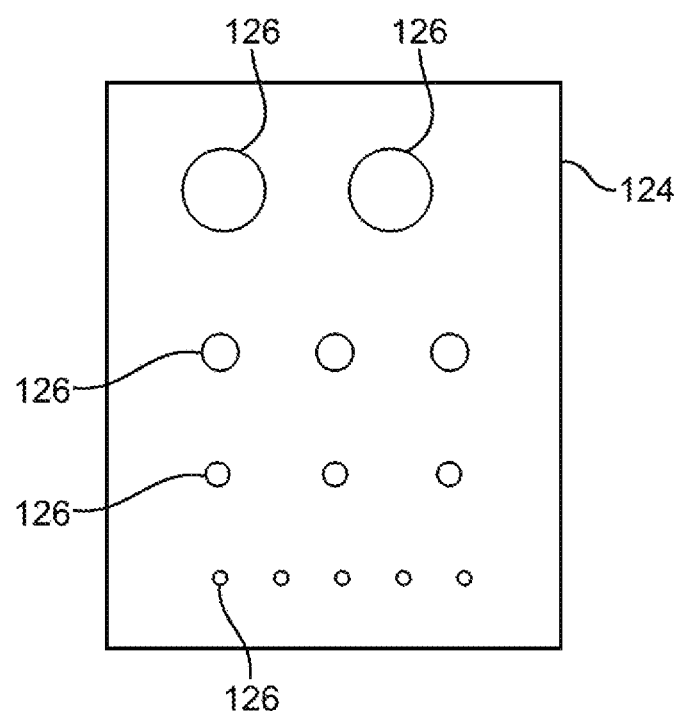
FIG. 21 is a top view of an illustrative moisture indicator structure having a moisture barrier layer with holes that lies between a wicking layer and a dye layer in accordance with an embodiment of the present invention.

A top view of an illustrative moisture barrier layer of this type is shown in FIG. 21. As shown in FIG. 21, moisture barrier layer 124 may have openings 126. Openings 126 may all have the same size or may have different sizes. Openings 126 of FIG. 21 are round, but this is merely illustrative. Any suitable shapes may be used for openings 126 if desired.

Openings 126 may be arranged within moisture barrier layer 124 so that some portions of moisture barrier layer 124 allow moisture to pass more readily than others.

Figure 22:
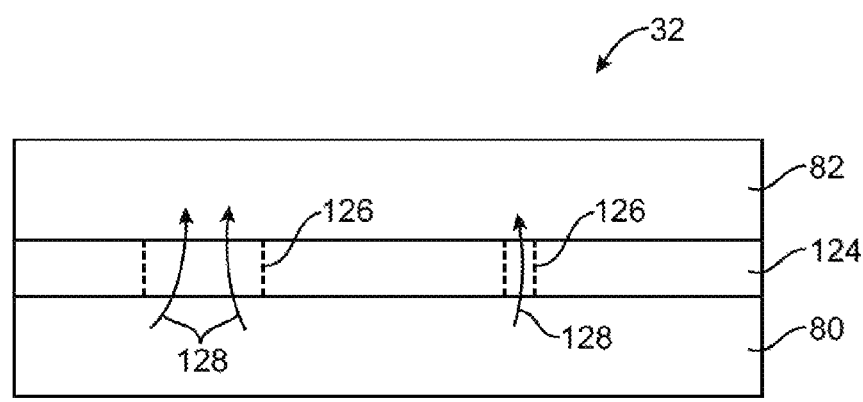
FIG. 22 is a side view of an illustrative moisture indicator structure having a moisture barrier layer with holes that lies between a wicking layer and a dye layer in accordance with an embodiment of the present invention.

A cross-sectional side view of a portion of a moisture indicator that has a perforated moisture barrier layer 124 of the type shown in FIG. 21 is shown in FIG. 22.

In the example of FIG. 22, moisture barrier layer 124 has been interposed between dye layer 80 and wicking layer 82. As indicated by arrows 128, dye may bleed through openings 126. Regions of layer 124 that are more porous (i.e., that have more openings and/or larger openings) will tend to be more sensitive to moisture than regions of layer 124 with fewer openings (and/or smaller openings). By adjusting the pattern of perforations in layer 124, the porosity of barrier layer 124 can be adjusted and moisture indicator 32 can be provided with regions having different moisture sensitivities. If desired, moisture barrier layers such as upper moisture barrier layer 86 and lower moisture barrier layer 78 can be provided with openings (e.g., in a pattern of perforations that allow moisture to enter moisture indicator 32 in some regions more readily than in others).

The foregoing is merely illustrative of the principles of this invention and various modifications can be made by those skilled in the art without departing from the scope and spirit of the invention.

What is claimed is:

1. A portable electronic device, comprising:
   a housing having an opening in an exterior surface of the housing; and
   a moisture indicator in the opening, wherein the moisture indicator comprises a wicking layer and a dye layer, wherein the entire wicking layer is overlapped by the dye layer, wherein the wicking layer has a first region with a first moisture sensitivity and has a second region with a second moisture sensitivity, and wherein the first moisture sensitivity is different than the second moisture sensitivity.

2. The portable electronic device defined in claim 1, wherein the moisture indicator comprises:
   a moisture barrier layer interposed between the wicking layer and the dye layer.

3. The portable electronic device defined in claim 2, wherein the moisture barrier layer comprises at least one opening.

4. The portable electronic device defined in claim 3, wherein the at least one opening comprises a pattern of openings that makes a first part of the moisture barrier layer more porous than a second part of the moisture barrier layer.

5. The portable electronic device defined in claim 3 wherein the at least one opening comprises at least a first hole in a first part of the moisture barrier layer and at least a second hole in a second part of the moisture barrier layer, and wherein the first hole covers a larger area of the moisture barrier layer than the second hole.

6. The portable electronic device defined in claim 3 wherein the at least one opening in the moisture barrier layer comprises a pattern of holes that allow water to pass more readily through a first part of the moisture barrier layer than through a second part of the moisture barrier layer.

7. The portable electronic device defined in claim 3 wherein the at least one opening extends from a first side of the moisture barrier layer to a second side of the moisture barrier layer.

8. A portable electronic device comprising:
   a housing having an opening in an exterior surface of the housing; and
   a moisture indicator in the opening, wherein the moisture indicator comprises:
   a dye layer;
   a first wicking layer formed adjacent the dye layer; and
   a second wicking layer that covers some but not all of the first wicking layer.

9. The portable electronic device defined in claim 8, wherein the first wicking layer overlaps the entire dye layer.

10. The portable electronic device defined in claim 8, wherein the moisture indicator further comprises a third wicking layer.

11. The portable electronic device defined in claim 10, wherein the third wicking layer covers some but not all of the second wicking layer.

12. The portable electronic device defined in claim 11, wherein the second wicking layer is in direct contact with the first wicking layer, and wherein the third wicking layer is in direct contact with the second wicking layer.

13. The portable electronic device defined in claim 8, wherein the moisture indicator further comprises first and second moisture barrier layers that are sealed together along at least one sealed edge of the moisture indicator.

14. The portable electronic device defined in claim 13, wherein the dye layer, the first wicking layer, and the second wicking layer are interposed between the first and second moisture barrier layers.

15. A portable electronic device comprising:
   a housing having an opening in an exterior surface of the housing; and
   a moisture indicator in the opening, wherein the moisture indicator comprises dye and a wicking layer formed adjacent the dye, wherein the wicking layer has a first portion with a first thickness and a second portion with a second thickness, wherein the first and second thicknesses are different, and wherein the wicking layer smoothly changes in thickness from the first thickness at the first portion to the second thickness at the second portion.

16. The portable electronic device defined in claim 15, wherein the entire wicking layer is adjacent the dye.

17. The portable electronic device defined in claim 8, wherein the dye layer overlaps the entire first wicking layer.

18. The portable electronic device defined in claim 17, wherein the second wicking layer is adjacent to and in direct contact with the first wicking layer.

19. The portable electronic device defined in claim 18, wherein the moisture indicator further comprises a third wicking layer that covers some but not all of the second wicking layer, wherein the third wicking layer is adjacent to and in direct contact with the second wicking layer, and wherein the second wicking layer is interposed between the first wicking layer and the third wicking layer.

20. The portable electronic device defined in claim 1, wherein the first region vertically overlaps the dye layer, wherein the second region vertically overlaps the dye layer, and wherein the first and second regions are not vertically overlapping.

* * * * *